United States Patent [19]

Grove et al.

[11] Patent Number: 5,569,667
[45] Date of Patent: Oct. 29, 1996

[54] TREATMENT OF PROSTATE CANCER

[75] Inventors: William R. Grove, Whitmore Lake; Wilbur R. Leopold, Ann Arbor, both of Mich.

[73] Assignee: Warner-Lambert Company, Morris Plains, N.J.

[21] Appl. No.: 524,912

[22] Filed: Sep. 8, 1995

Related U.S. Application Data

[63] Continuation of Ser. No. 375,089, Jan. 19, 1995, abandoned.

[51] Int. Cl.⁶ ................................................. A61K 31/415
[52] U.S. Cl. ................................................. 514/403
[58] Field of Search ................................. 514/403

[56] References Cited

U.S. PATENT DOCUMENTS 4,604,390  8/1986  Elslager et al. .......................... 514/222

Primary Examiner—Jerome D. Goldberg
Attorney, Agent, or Firm—Charles W. Ashbrook

[57] ABSTRACT

Prostate cancer is treated with 5-[(2-aminoethyl)amino]-2-[2-(diethylamino)ethyl]-2H-[1]benzothiopyrano-[4,3,2-cd]indazol-8-ol or a pharmaceutically acceptable salt thereof.

3 Claims, No Drawings

TREATMENT OF PROSTATE CANCER

This application is a continuation of Ser. No. 08/375,089, filed Jan. 19, 1995, now abandoned.

FIELD OF THE INVENTION

This invention provides a method for treating prostate cancer comprising administering to a subject in need of treatment an effective amount of 5-[(2-aminoethyl)amino]-2-[2-(diethylamino)ethyl]-2H-[1]benzothiopyrano[4,3,2-cd]indazol-8-ol, or a pharmaceutically acceptable salt thereof.

BACKGROUND OF THE INVENTION

Prostate cancer is the most commonly occurring tumor in men. It is an adenocarcinoma that is second only to lung cancer in mortality. Prostate cancer currently accounts for about 35000 deaths each year in the United States alone. The incidence increases with age, and because there is an increasing number of men who are older than 50 years, when prostate cancer is often first diagnosed, the total number of cases increases yearly. Data compiled from the Centers for Disease Control National Center for Health Statistics report an alarming increase in the incidence of the disease since 1980 in the US. Carter, et al., estimated that during the next 8 to 10 years, prostate cancer cases will increase by 90%, and deaths from prostate cancer will increase by 37%; *Prostate* 1990;16:39–48.

Localized treatment with surgery and/or radiotherapy are curative in many patients whose disease is diagnosed early. However, up to 40% of patients with advanced disease, and a large proportion of all patients, eventually develop metastatic disease following localized therapy. Treatment for advanced disease initially involves hormonal manipulations and palliative radiotherapy. These strategies have proven to be of marked clinical benefit in terms of symptomatic relief, but have not resulted in long-term disease-free survival. The use of cytotoxic agents in the management of hormone-resistant advanced prostate cancer remains poorly defined. A few single agents have become "standard therapy", although demonstration of their efficacy, by contemporary standards, is lacking.

Combination chemotherapy is frequently employed, although its contribution to overall patient management is largely unsubstantiated, especially when critical assessment of efficacy parameters are used. Newer approaches using chemohormonal therapy and hormonal priming therapies have failed. High-dose chemotherapy with transplant regimens are not well-tolerated in an elderly population, to which most men suffering from prostate cancer belong. A growth factor inhibitor, suramin, has shown promising initial results. However, no therapy to date has been demonstrated to improve overall survival in patients with advanced hormone refractory prostate cancer.

Accordingly, a strong need continues to find new agents that can be utilized to treat prostate cancer. We have now discovered that 5-[(2-aminoethyl)amino]- 2-[2-diethylamino)ethyl]-2H-[1]benzothiopyrano-[4,3,2-cd]indazol-8-ol is effective clinically to treat prostate cancer. The compound, and its pharmaceutically acceptable salts, will be referred to herein as BTPI, referring to benzothiopyranoindazol.

BTPI is disclosed in U.S. Pat. No. 4,604,390. The compound is one of a large group of indazoles which are said to have antibacterial, antifungal, and antineoplastic activities. Data is present in the patent showing in vitro activity against L1210 and P388 murine leukemia cell lines. Because few oncolytic agents are effective in treating prostate cancer, and because in vitro activity against murine leukemia cell lines is not predictive of activity against prostate cancer, it is surprising that BTPI is clinically efficacious against prostate cancer.

An object of this invention is, therefore, to provide a new treatment for prostate cancer utilizing BTPI.

SUMMARY OF THE INVENTION

This invention provides a method for treating prostate cancer comprising administering to a subject in need of treatment an effective amount of 5-[(2-aminoethyl)amino]-2-[2-(diethylamino)ethyl]-2H-[1]benzothiopyrano[4,3,2-cd]indole-8-ol, or a pharmaceutically acceptable salt thereof, collectively referred to herein as BTPI.

In a preferred embodiment, the compound to be utilized in the method of this invention will be employed as a pharmaceutically acceptable acid addition salt, ideally as the trihydrochloride.

In another preferred embodiment, the invention provides a method of treating hormone-refractory adenocarcinoma of the prostate comprising administering to a male in need of treatment an effective amount of BTPI.

DETAILED DESCRIPTION OF THE INVENTION

In accordance with this invention, BTPI will be prepared according to the method of U.S. Pat. No. 4,604,390, which is incorporated herein by reference. BTPI will be formulated for convenient administration by the oral or parenteral routes, and preferably will be administered intravenously. BTPI generally is synthesized as a white crystalline powder, or alternatively can be produced as a lyophilized powder for convenient reconstitution, for example, in water, isotonic saline, or 5% dextrose solution. The compound can be admixed with common pharmaceutical excipients such as magnesium carbonate, sodium ascorbate, methylcellulose, sodium carboxymethylcellulose, and bulking agents such as mannitol and the like.

As noted above, the compound can be utilized as a pharmaceutical salt, which can be prepared by reacting the free amino base compound with an organic or inorganic acid such as those commonly used in the pharmaceutical field. Typical acids include hydrochloric acid, phosphoric acid, sulfuric acid, acetic acid, ascorbic acid, tartaric acid, maleic acid, and the like.

The compound is preferably utilized as the trihydrochloride salt.

BTPI, in the form of the trihydrochloride, is freely soluble in water (over 100 mg/mL) and in aqueous buffers over a pH range of about 1.5 to 6. In a preferred embodiment, BTPI is formulated for IV injection. A preferred form of bulk BTPI is as a lyophilized white powder.

For clinical use, BTPI can be supplied as a lyophilized powder for reconstitution, for instance, it can be packaged in 10-cc amber glass vials. Each vial will contain, for example, 250 mg BTPI base (as trihydrochloride), sodium ascorbate (antioxidant), sodium dihydrogen phosphate and disodium hydrogen phosphate (for pH adjustment), and mannitol (as a bulking agent). When reconstituted with 5 mL of Water for Injection (USP), the resulting solution will contain 50 mg/mL of BTPI base.

Lyophilized BTPI for injection is projected to be physically and chemically stable for at least 12 months when stored at room temperature or lower, ideally at about 4° C.

The solution reconstituted with 5 mL of Water for Injection, USP, is chemically and physically stable for 8 hours at room temperature. The pH of the reconstituted solution is about 4.5. The lyophilized powder is reconstituted with Water for Injection, USP, and then diluted with 5% Dextrose for Injection, USP, to a concentration of 2.0 to 6.2 mg/mL. The resulting admixture is chemically and physically stable for up to 24 hours when kept in glass bottles or Excel bags.

In practicing this invention, an effective dose of BTPI will be administered to a subject diagnosed as having prostate cancer and in need of treatment. An "effective dose" is that amount of BTPI which has a beneficial therapeutic effect against the tumor without unacceptably high degree of adverse events. A typical effective dose will be from about 100 mg/m$^2$ to about 1000 mg/m$^2$, and preferably about 500 mg/m$^2$ to about 800 mg/m$^2$. Such doses will be administered once every 2 to 3 weeks, or as otherwise dictated by the attending physician.

The efficacy of BTPI against prostate tumors has been evaluated and proven in well-controlled clinical trials.

BTPI is undergoing a Phase 2 clinical evaluation. The compound is being evaluated in a nonrandomized, noncomparative, open-label Phase 2 trial of BTPI in patients with advanced prostate cancer. Patients received treatment courses consisting of single doses of BTPI every 3 weeks. The primary efficacy end point is the determination of response to treatment measured either by objective parameters or by change in prostatic specific antigen (PSA) level. The trial will be carried out on from 30 to 44 patients.

To be included in the clinical evaluation of BTPI, patients must meet all of the following criteria:

Advanced (i.e., metastatic; Stage D2) histologically confirmed hormone-refractory adenocarcinoma of the prostate;

No prior cytotoxic chemotherapy. For the purposes of this trial, estramustine phosphate will be considered as a cytotoxic chemotherapy agent, but biologic agents will not be considered as cytotoxic chemotherapy;

At least 18 years old;

Performance status of 0, 1, or 2 determined within 1 week prior to the first treatment;

Expected survival of over 9 weeks;

Adequate renal, liver, and bone marrow function, obtained within 1 week prior to the first treatment, defined as: serum creatinine, total bilirubin, and SGOT values $\leq 1.5$ times the upper limit of normal; absolute granulocyte count $\geq 1,500$/mm$^3$, platelet count $\geq 100,000$/mm$^3$. Serum testosterone level $<100$ ng/dL obtained within 2 weeks prior to the first treatment; and, If present, bidimensionally measurable lesions that have NOT been irradiated. If patient does not have measurable disease, the patient must have a PSA level $>20$ ng/mL.

Patients with any of the following conditions are excluded from the study:

Radiation therapy within 3 weeks or flutamide therapy within 2 weeks prior to treatment with BTPI. In patients who have been receiving flutamide at the time of progression, PSA values 2 weeks after discontinuation of flutamide must be increasing or stable ($\pm 10\%$ of value while on flutamide);

Concurrent cancer chemotherapy, immunotherapy, radiotherapy, or surgery;

Major surgery within the previous 14 days;

Concurrent serious infection;

Life-threatening illness (unrelated to tumor) requiring therapy, including significant cardiovascular disease;

Any of the following cardiac risk factors: active congestive heart failure; uncontrolled angina; myocardial infarction in the 6 months prior to entry; left ventricular ejection fraction (LVEF) $<45\%$, obtained within 3 weeks prior to first treatment;

History of any other cancer (except nonmelanoma skin cancer), unless in complete remission and off of all therapy for that disease for a minimum of 3 years;

Confirmed or suspected brain metastases; and/or,

Overt psychosis or mental disability or otherwise incompetent to give informed consent.

All patients who receive at least 1 complete course of therapy (defined as having received the intended dose of BTPI during the first course of therapy and having at least 1 response assessment) will be evaluated for efficacy.

The schedule for response assessments depends on the method(s) being used to follow the sentinel lesions.

Response evaluations performed by physical examination and a PSA determination will be done at the end of each course of therapy. Response evaluations performed by x-ray techniques, bone scans, or by CT-scans will be done at the end of every 2 courses of therapy, except when needed to make the initial 28-day confirmatory assessment of partial response (PR) or complete response (CR). Once a PR or CR is confirmed, repeat response evaluations will be done after every 2 courses for physical examination or x-ray techniques, or 3 courses by CT-scans, to document response duration.

Patients who have therapy discontinued while maintaining a CR or PR will be re-evaluated for duration of response every 2 months until recurrence or progression is documented.

The primary efficacy parameter will be objective evidence of change in the size of the sentinel lesion(s) or change in the PSA level, and categorized as a CR, PR, stable disease (SD), or progressive disease (PD).

The secondary efficacy parameters will be duration of response, time to response, time to progression, and survival.

BTPI has shown excellent antitumor activity in several patients who have undergone clinical treatment. In preliminary stages of the trial, eleven patients are receiving treatment with BTPI; 4 patients were terminated from the trial; 2 patients have shown excellent responses; and, a third continues to show marked improvement.

For example, 1 patient was a 57-year-old man (JM) with disseminated bone disease and a rising PSA following hormone deprivation therapy. The disease was classified as Stage D2, metastatic to bones and retroperitoneal lymph nodes as evidenced by bone scan done prior to treatment with BTPI. The patient had failed prior hormonal therapy with flutamide and Megace™. His baseline PSA level was 39.8 ng/mL. The patient received 8 treatment courses of BTPI over a 146-day period. PSA levels decreased substantially after each course of BTPI, and reached normal levels after 3 courses of treatment. A bone scan after the second course of treatment with BTPI established a decreased intensity of uptake in metastatic disease sites in his scapula, sacroiliac joint, and skull. Another bone scan done after the fourth course of treatment showed a decreased intensity of uptake in metastatic disease sites in the thoracic and lumbar spine, sacroiliac joint, and scapula. The patient had no disease-related symptoms following the eighth course of treatment, his performance status was normal, and his PSP value continued in the normal range ($\leq 4.0$ ng/mL). Further treatment was suspended, after which the patient continued to feel well and exhibit improvement for 4 months. His duration of positive response measured by PSA levels continued for 7 months following suspension of treatment. His duration of progression-free survival from the start of treatment with BTPI was approximately 8 months. He then developed symptoms of progressive bone disease in his spine and began radiation treatment to the spinal cord.

Table I below shows the PSA levels for the above patient, measured over a 10-month period. The asterisks indicate the days on which BTPI was administered and the dosage in mg/m$^2$.

TABLE I

| Day of Trial | BTPI mg/m$^2$ | PSA Level (ng/mL) |
| --- | --- | --- |
| 1 | *700 | 39.8 |
| 22 | *825 | 20.5 |
| 43 | *875 | 8.3 |
| 64 | *700 | 3.8 |
| 85 | *700 | 2.4 |
| 106 | *700 | 1.2 |
| 123 | *700 | 0.9 |
| 146 | *700 | 0.5 |
| 167 |  | 0.7 |
| 185 |  | 1.2 |
| 223 |  | 2.4 |
| 248 |  | 3.9 |
| 278 |  | 9.4 |
| 304 |  | 8.3 |

A second patient was a 69-year-old man (JD) diagnosed with adenocarcinoma of the prostate. His disease stage was D2, being metastatic to bones and abdominal lymph nodes. Prior hormonal therapy with flutamide and leuprolide had failed. At the time of starting therapy with BTPI, he was suffering tumor-related symptoms of pain, impaired bowel function, and decreased performance status. He had a colostomy to relieve symptoms of gastrointestinal tract compression from enlarged lymph nodes. His baseline PSA level was 358.4 ng/mL (normal value <4.0 ng/mL). He had an additional CT-scan and a bone scan done prior to starting treatment with BTPI to document his widespread tumor involvement.

Over a 6-month period, the patient received 8 treatment courses of BTPI (about 500 to about 700 mg/m$^2$). After the first 2 courses had been completed, his PSA level decreased to 231 ng/mL. After he completed 4 courses of BTPI treatment, a repeat abdominal CT-scan was done which established a reduction in the size of his diseased lymph nodes. His PSA levels continued to drop. Further reduction in the size of abdominal lymph nodes was shown by a CT-scan taken after 6 doses of BTPI, and complete resolution of lymph node disease was observed by CT-scan after 8 courses of treatment. A repeat bone scan was done which showed definite improvement in his bone lesions. Further treatment with BTPI was suspended because the patient showed no disease-related symptoms, his performance status was significantly improved, and his PSA level was continuing to drop. A CT-scan done 7 weeks after treatment with BTPI was stopped showed no evidence of disease. The patient continued to feel well for approximately 6 months after treatment with BTPI was suspended. His duration of response was about 9 months when measured by reduced PSA levels. His duration of progression-free survival from the start of treatment with BTPI was 11 months. Treatment with BTPI resumed when PSA levels started increasing.

The Table II below shows PSA levels for the above patient measured over a course of about 1 year. The asterisk indicates the days on which BTPI was administered and the dosage in mg/m$^2$.

TABLE II

| Day of Trial | BTPI mg/m$^2$ | PSA Level (ng/mL) |
| --- | --- | --- |
| 1 | *700 | 358.4 |
| 22 | *525 | 553.0 |
| 41 | *656 | 231.0 |
| 64 | *656 | 118.1 |
| 90 | *656 | 73.0 |
| 113 | *656 | 30.7 |
| 132 | *656 | 23.7 |
| 155 | *656 | 14.7 |
| 171 |  | 9.9 |
| 211 |  | 5.8 |
| 239 |  | 3.9 |
| 267 |  | 8.5 |
| 289 |  | 19.1 |
| 316 |  | 51.5 |
| 330 |  | 70.9 |
| 358 |  | 116.0 |

Table III shows the PSA levels of another patient (DC) after receiving only 4 courses of treatment with BTPI.

TABLE III

| Day of Trial | PSA Level (ng/mL) |
| --- | --- |
| 1 | 148.0 |
| 21 | 65.5 |
| 28 | 67.3 |
| 35 | 37.7 |

Table IV shows the PSA levels of a patient (PF) after receiving 5 doses of BTPI.

TABLE IV

| Day of Trial | PSA Level (ng/mL) |
| --- | --- |
| 1 | 89.7 |
| 25 | 55.9 |
| 48 | 36.6 |
| 64 | 47.8 |
| 90 | 48.2 |

These and similar clinical results establish BTPI is an effective treatment for prostate cancer, and is particularly effective in treating hormone refractory prostate cancer. BTPI is well-tolerated, with few adverse side effects. Accordingly, BTPI is an excellent agent for treating prostate cancer.

What is claimed is:

1. A method for treating prostate cancer comprising administering to a subject in need of treatment an effective dose of 5-[(2-aminoethyl)amino]-2-[2-(diethylamino)ethyl]-2H-[1]benzothiopyrano-[4,3,2-cd]indazol-8-ol or a pharmaceutically acceptable salt thereof.

2. A method according to claim 1 wherein the prostate cancer being treated is hormone refractory prostate cancer.

3. A method according to claim 2 wherein the compound utilized is 5-[(2-aminoethyl)amino]-2-[2-(diethylamino)ethyl]-2H-[1]benzothiopyrano[4,3,2-cd]-indazol-8-ol trihydrochloride.

* * * * *